US007731570B2

(12) United States Patent
Groman

(10) Patent No.: US 7,731,570 B2
(45) Date of Patent: Jun. 8, 2010

(54) MICRO-ABRASIVE BLASTING DEVICES WITH PERTURBATION CONTROL

(76) Inventor: Boaz Barry Groman, 7485 Malibu Crescent, Boca Raton, FL (US) 33433

( * ) Notice: Subject to any disclaimer, the term of this patent is extended or adjusted under 35 U.S.C. 154(b) by 1383 days.

(21) Appl. No.: 11/077,098

(22) Filed: Mar. 10, 2005

(65) Prior Publication Data

US 2006/0205330 A1    Sep. 14, 2006

(51) Int. Cl.
B24C 3/00    (2006.01)
(52) U.S. Cl. .......................................... 451/90; 451/99
(58) Field of Classification Search .................. 451/90, 451/102, 101, 38, 39, 99
See application file for complete search history.

(56) References Cited

U.S. PATENT DOCUMENTS

| | | | |
|---|---|---|---|
| 2,133,149 A | 10/1938 | Poncelet | |
| 2,441,441 A | 9/1948 | Paasche | |
| 2,577,465 A | 12/1951 | Jones et al. | |
| 2,612,732 A | 10/1952 | Ziegler | |
| 2,641,087 A | 6/1953 | Greiser | |
| 2,696,049 A | 12/1954 | Black | |
| 2,696,669 A | 12/1954 | Ikse | |
| 2,725,684 A | 12/1955 | Crowe | |
| 2,744,361 A | 5/1956 | Larson et al. | |
| 3,164,153 A * | 1/1965 | Zorzi | 433/88 |
| 3,626,841 A | 12/1971 | Schachter | |
| 3,631,631 A | 1/1972 | Greenstein | |
| 3,964,509 A | 6/1976 | Daubenberger et al. | |
| 3,981,479 A | 9/1976 | Foster et al. | |
| 4,032,474 A | 6/1977 | Goudriaan et al. | |
| 4,174,571 A | 11/1979 | Gallant | |
| 4,287,812 A | 9/1981 | Iizumi | |
| 4,369,607 A | 1/1983 | Bruggeman et al. | |
| 4,391,590 A | 7/1983 | Dougherty | |
| 4,475,370 A | 10/1984 | Stark et al. | |
| 4,646,782 A | 3/1987 | Ezekoye | |
| 4,673,051 A | 6/1987 | Darling et al. | |
| 4,941,298 A | 7/1990 | Fernwood et al. | |
| 4,967,791 A | 11/1990 | Sternberger | |
| 5,123,206 A | 6/1992 | Woodson | |
| 5,160,547 A | 11/1992 | Kirschner et al. | |
| 5,197,876 A | 3/1993 | Coston | |
| 5,199,229 A | 4/1993 | Herold | |

(Continued)

FOREIGN PATENT DOCUMENTS

GB            832231            4/1960

OTHER PUBLICATIONS

Prepmaster User Instructions, copr 2004.

(Continued)

*Primary Examiner*—Dung Van Nguyen
(74) *Attorney, Agent, or Firm*—Gerald E. Linden; Dwight A. Stauffer

(57) ABSTRACT

The present invention is a micro-abrasive blasting device (55) with superior perturbation control via a plurality of delivery conduits (25) of various lengths and apertures. The user is able to individually open and close bypass conduit pinch valve (99) external to micro-abrasive blasting device (55) to affect the perturbation intensity internal to the mixing chamber (23). By selectively opening and closing flow through delivery conduits (25) it is possible to provide a more consistent perturbation rate and select the perturbation intensity internal to mixing chamber (23).

10 Claims, 12 Drawing Sheets

U.S. PATENT DOCUMENTS

| | | | |
|---|---|---|---|
| 5,261,459 | A | 11/1993 | Atkinson et al. |
| 5,289,919 | A | 3/1994 | Fischer |
| 5,330,354 | A | 7/1994 | Gallant |
| 5,368,844 | A | 11/1994 | Gaffar et al. |
| 5,396,292 | A | 3/1995 | Murata |
| 5,839,946 | A | 11/1998 | Hertz |
| 6,004,191 | A | 12/1999 | Schur et al. |
| 6,024,566 | A | 2/2000 | Bruns et al. |
| 6,083,001 | A | 7/2000 | Deardon et al. |
| 6,093,021 | A | 7/2000 | Rainey |
| 6,099,306 | A * | 8/2000 | Lawler ......................... 433/88 |
| 6,287,180 | B1 | 9/2001 | Hertz |
| 6,293,856 | B1 | 9/2001 | Hertz et al. |
| 6,343,717 | B1 | 2/2002 | Zhang et al. |
| 6,347,984 | B1 | 2/2002 | Groman |
| 6,354,924 | B1 | 3/2002 | Trafton et al. |
| 6,398,628 | B1 | 6/2002 | Groman |
| 6,439,966 | B2 | 8/2002 | Bruns et al. |
| 6,951,505 | B2 * | 10/2005 | Hertz ......................... 451/38 |
| 7,101,265 | B1 * | 9/2006 | Schur et al. ................... 451/90 |
| 7,226,342 | B2 * | 6/2007 | Hertz ......................... 451/90 |
| 2002/0077041 | A1 | 6/2002 | Groman |
| 2003/0003849 | A1 | 1/2003 | Groman |
| 2006/0252006 | A1 | 11/2006 | Apelker et al. |
| 2007/0287126 | A1 | 12/2007 | Groman |

OTHER PUBLICATIONS

Air Abrasion Industry, copr 2003.

* cited by examiner

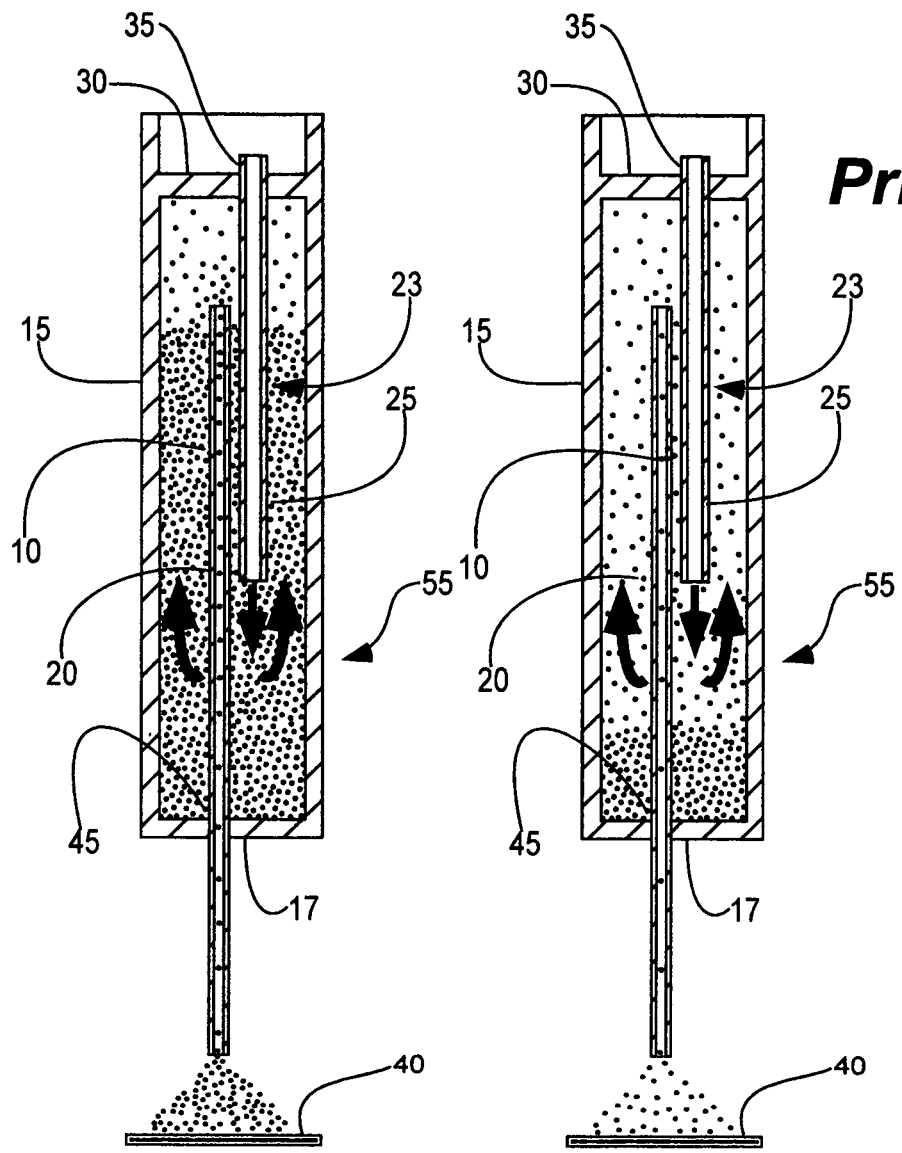
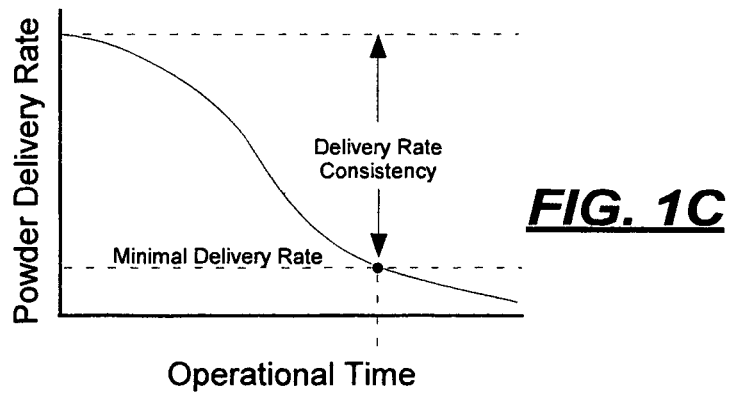
FIG. 1A  FIG. 1B
FIG. 1C

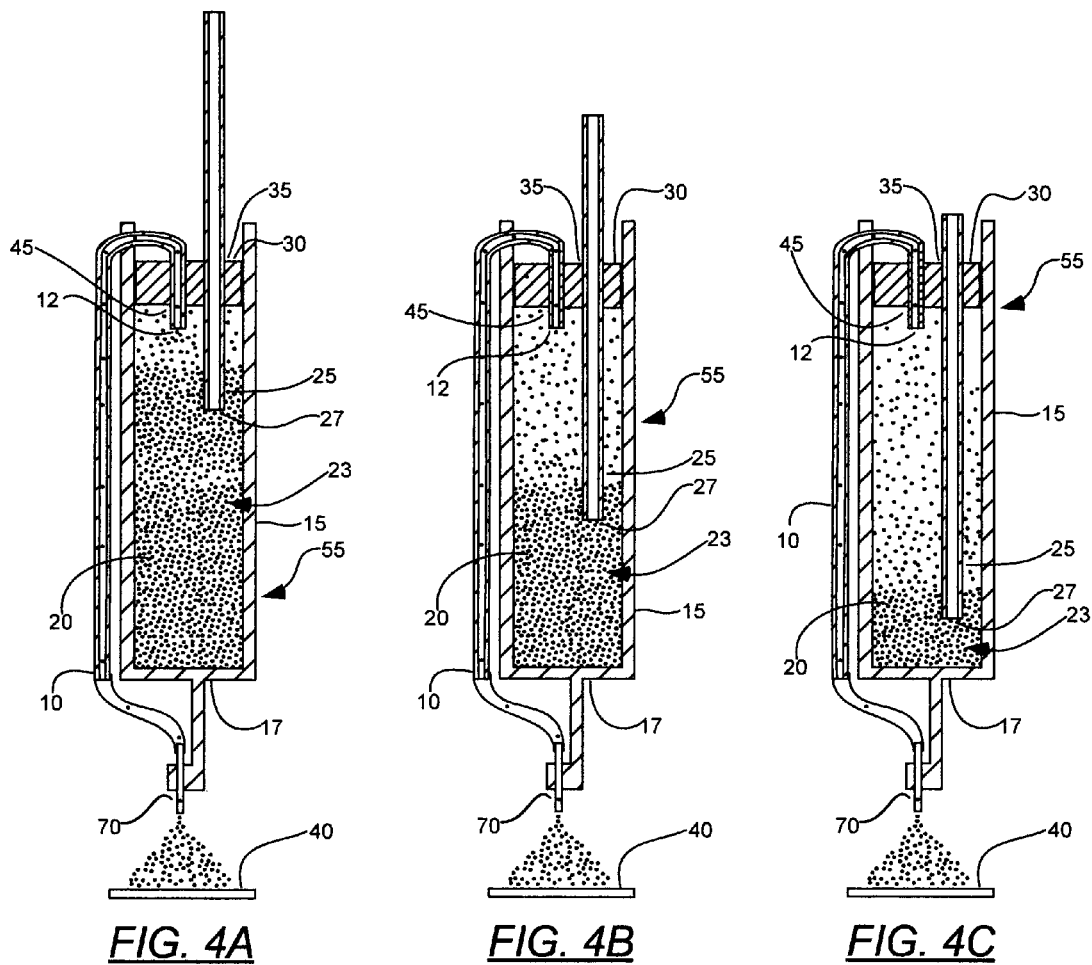
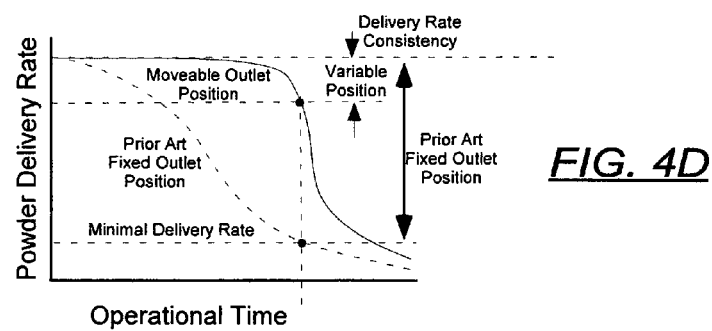
FIG. 4A  FIG. 4B  FIG. 4C
FIG. 4D

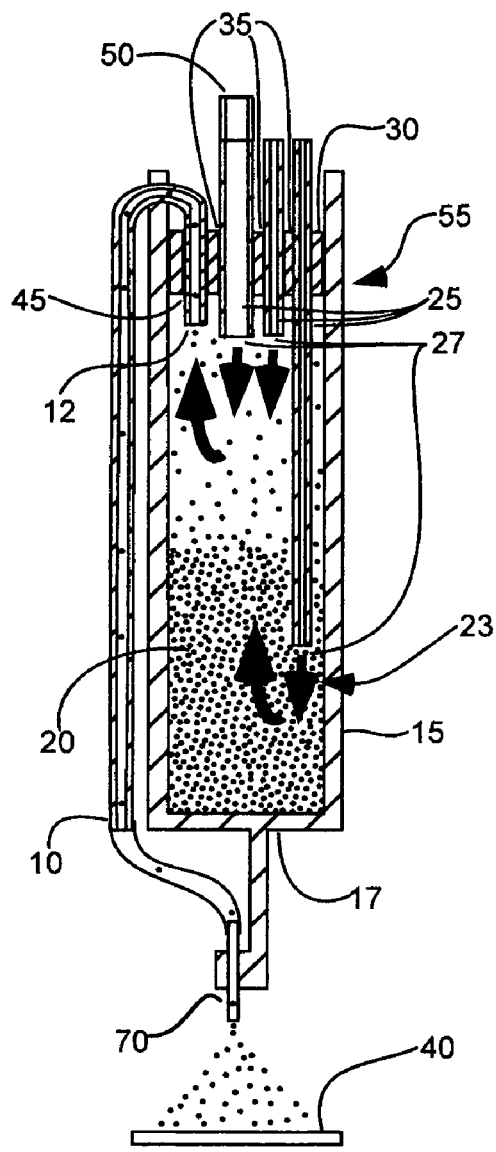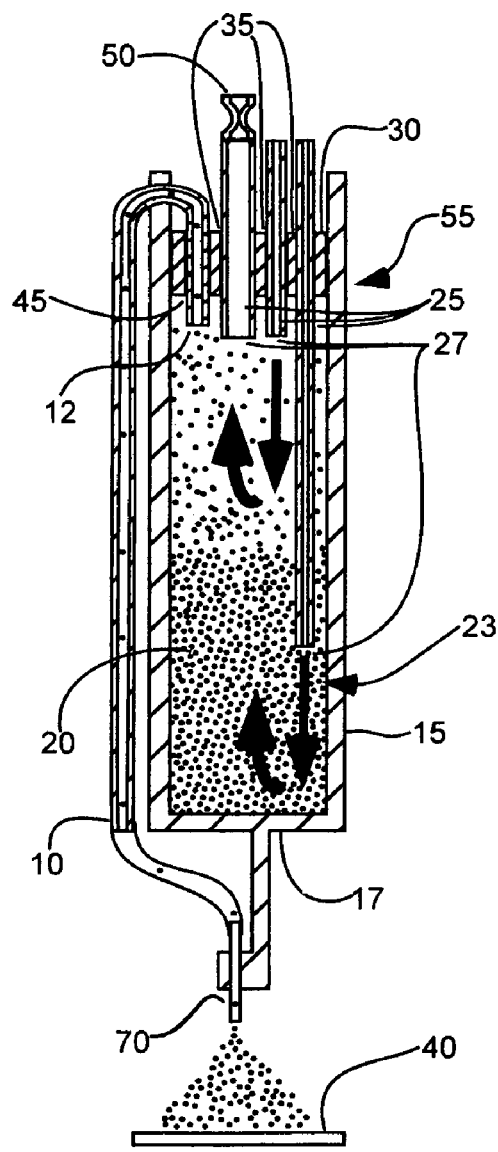
*FIG. 10A*  *FIG. 10B*

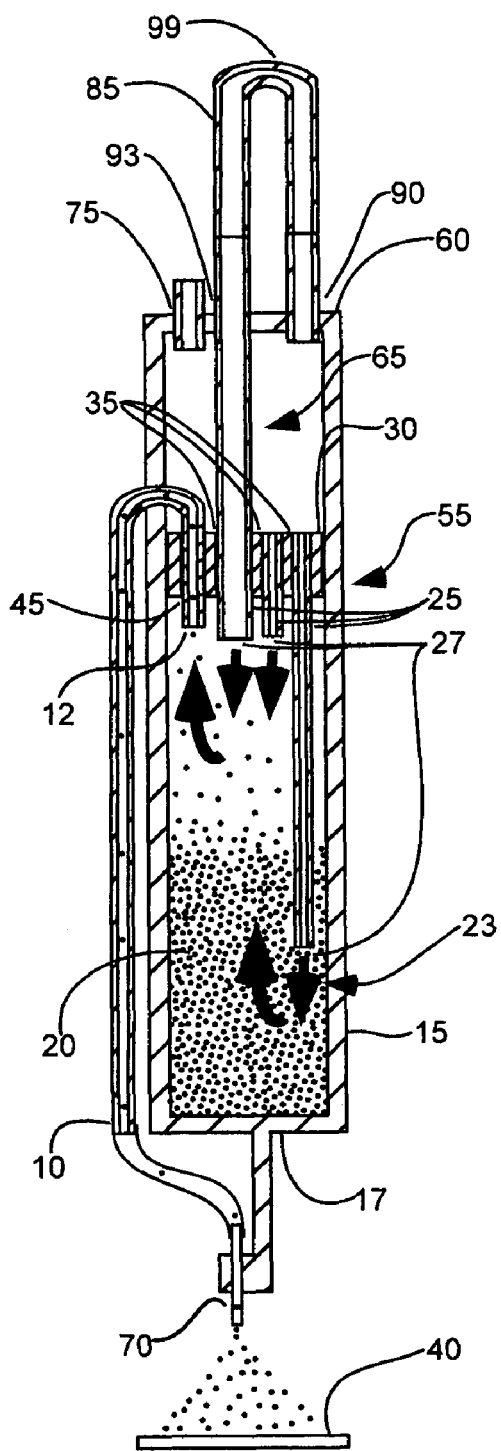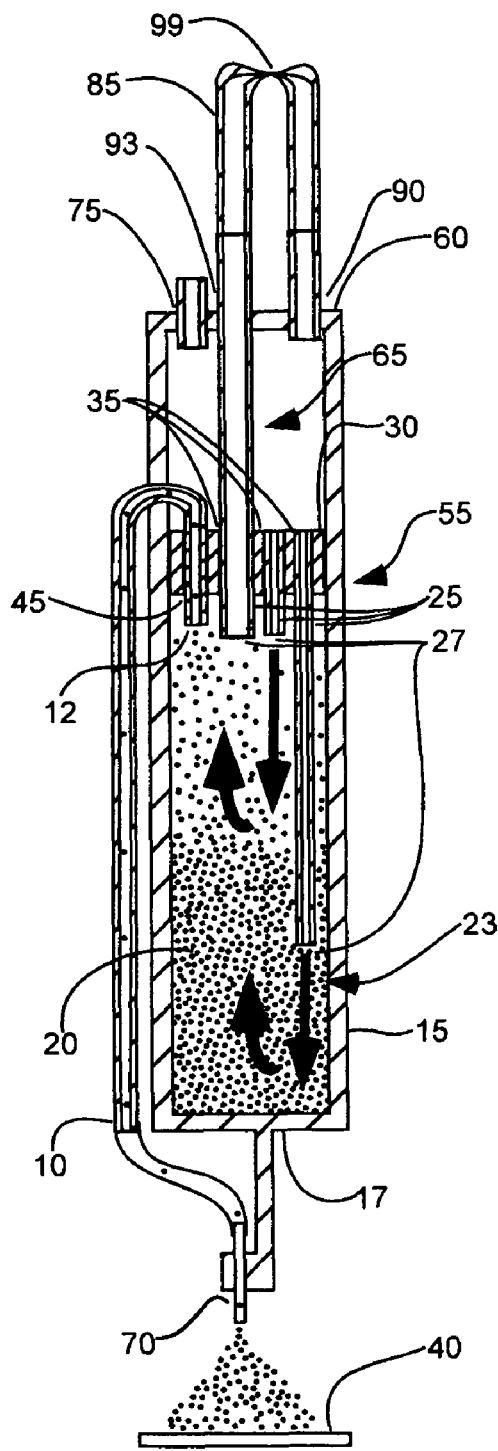
*FIG. 12A*  *FIG. 12B*

MICRO-ABRASIVE BLASTING DEVICES WITH PERTURBATION CONTROL

BACKGROUND OF THE INVENTION

The present invention relates generally to the field of devices for propelling abrasive powder with intent to etch the surface of a target material. More specifically, the present invention relates to a micro-abrasive blasting device powered by a pressurized-gas source for use with dental procedures.

Abrasive blasting devices operate on the physical property that gas at a higher pressure flows towards and into gas at lower pressure. When abrasive powder is mixed with gas at higher pressure, the gas carries the abrasive powder as the gas accelerates and flows to the lower pressure. As the gas and abrasive powder blast the target material at high speed, the impact of the particles removes layers of the target material.

This process of material removal is commonly known as etching and also as sandblasting. As the rate of the target material removal increases, the etching process can be utilized for drilling and cutting. More specifically, the aggressiveness of the particulate impact-speed and frequency determine the rate of material removal, and thus whether an abrasive blasting device is useful for polishing, etching, or drilling. Particulate impact-speed and impact-frequency are adjusted by variation of the gas flow rate and gas-to-particulate mixture ratio through perturbation of the abrasive material.

In dentistry this technology is known as micro-abrasion and is used to achieve a variety of goals—such as to remove foreign material or to dull a shiny surface, roughen or etch the surface to enhance bonding quality and to remove decay by drilling and cutting tooth structure. To facilitate such procedures, it is of supreme importance to select the precise quantity of abrasive powder introduced into the gas stream. As the rate of powder delivery or concentration of abrasive in the gas stream is increased, the greater the cutting rate of the device. So for procedures that only require light etching, a reduced amount of abrasive particles must be present in the gas stream, while for drilling and cutting procedures elevated quantities of abrasive particles in the gas stream provide for most efficient operation. Such delicate procedures performed intra-oral require instantaneous response and precise control over the flow of the particle stream to prevent damage due to over-etching.

Once the dentist has selected the abrasive concentration, it is of equal importance for the device to maintain a consistent powder delivery rate. Significant damage can be caused by an unexpected increase or decrease in particulate concentration during an intra-oral procedure. Over-etching of a tooth surface due to an increase in abrasion rate leads to permanent tooth damage. Under etching of a tooth surface due to a decrease in abrasion rate may cause weak bonding and/or trapped bacteria under the sealants.

Most air abrasion devices provide complex mechanisms to allow adjustment and assure the consistency of the abrasive concentration introduced into the air stream. Deardon et al. U.S. Pat. No. 6,083,001 discloses a dental air abrasion system in which the flow of the particles is electronically controlled by pressure differentials. Rainey U.S. Pat. No. 6,093,021 discloses an automated control system which utilizes a gas stream mounted particulate sensor to regulate fluid flow rates into and around the ultrasonically agitated mixing chamber in order to accurately maintain the abrasive concentration in the air stream.

Simple self-contained air abrasion devices—such as by Stark et al., U.S. Pat. No. 4,475,370, Hertz, U.S. Pat. Nos. 5,839,946 and 6,287,180, Hertz PCT application 96/11696 filed on Jul. 15, 1996, Hertz et al. U.S. Pat. No. 6,293,856, Schur et al. U.S. Pat. No. 6,004,191, Trafton et al. U.S. Pat. No. 6,354,924, and Groman U.S. Pat. No. 6,398,628 and U.S. Pat. No. 6,347,984—rely on the air stream to perturb the abrasive and generate the mixing action. The etching rate of these devices is adjustable only by the inlet pressure for a given nozzle aperture, since it is the flow rate of the air stream that generates the powder perturbation. The greater the inlet pressure, the greater the gas flow rate through the device and thus the increase in abrasive delivery rate. Conversely low powder delivery rates are attained by reduction of the inlet gas pressure.

For these devices however, as the inlet pressure is reduced the flow rate through the device is reduces and so does the impact speed of the abrasive powder. The reduction in impact speed leads to a reduction in operational efficiency, since the lower impact speed of the particulates requires more operational time and a greater quantity of powder material to accomplish a task. Therefore, operation of light etching is achieved only at lower operational pressures and therefore lower particulate velocities. Additionally, since these self-contained devices utilize the inlet pressure for concentration selection, they only perform at their optimum efficiency at the maximum inlet pressure.

Additionally, self-contained air abrasion devices contain a preset amount of powder material within the mixing chamber. The operational time of the device is the time period during which powder is contained within the mixing chamber. In practice, the operational time of the device is defined to terminate when the powder delivery rate reaches such a low level that the device is not able to perform useful etching.

Self-contained air abrasion devices experience a change in the powder delivery rate as the contained abrasive is depleted from the mixing chamber. As the abrasive discharges from the mixing chamber, the location of the delivery conduit outlet changes with respect to the remaining powder material. When the prior art device shown in FIG. 1A initiates operation, the delivery conduit outlet is submerged within the abrasive material. But as the quantity of abrasive is reduced during operation, the discharge conduit outlet becomes more distant from the abrasive material, as shown in FIG. 1B. As the distance between the outlet and the powder material increases, less powder material is perturbed by the inlet air stream and thus less material introduced into the air steam.

FIG. 1C depicts the powder delivery rate for this prior art device over its operational time for a constant pressure air supply. Over the device's operational time the powder delivery rate decreases as the powder depletes from the device and the distance between the abrasive powder and the delivery conduit outlet increases. This leads to a decrease in perturbation of the powder material as the gas flow is further from the powder material. The device's operational time terminates when it no longer has a powder delivery rate capable of performing useful etching of the target material. FIG. 1C shows that this device has a large variation in powder delivery rate consistency. At the initial operational state powder delivery occurs at high rate and then rapidly decreases as the mixing chamber depletes of powder material.

The length of the delivery conduit is also a significant factor in the powder delivery rate. FIG. 2 depicts two configurations of prior art devices with fixed length delivery conduits. FIG. 2A illustrates a prior art device with a long delivery conduit that reaches deep into the powder material. Referring to FIG. 2C, this prior art device has a high powder delivery rate that rapidly depletes the quantity of powder material in the mixing chamber. The rapid depletion leads to a short operational time and a high variability in powder delivery rate. FIG. 2B illustrates a prior art device with a short delivery conduit that may be initially submerged in the powder material. Such a prior art device has a lower powder delivery rate that slowly depletes the quantity of powder material in the mixing chamber. The slow depletion leads to a longer operational time and a slower variability in powder delivery rate. As FIG. 2C illustrates, a short delivery conduit configuration provides lower capability to generate high powder perturbation and therefore always yields a lower powder delivery rate. Since the powder delivery rate is reduced, the operational time of the device is longer and the change of powder delivery rate is reduced, however, it is not capable of creating high powder delivery rates.

Powder perturbation rate is also affected by the diameter of the delivery conduit or its outlet aperture. Delivery conduit outlets with small apertures lead to high air velocities into the mixing chamber, while delivery conduit outlets with large apertures lead to low air velocities into the mixing chamber. FIG. 3 depicts two configurations of prior art devices with small and large delivery conduit diameters. FIG. 3A depicts a prior art device with a small diameter delivery conduit. FIG. 3C illustrates that a delivery conduit outlet with small aperture has a high powder delivery rate that rapidly depletes the quantity of powder material in the mixing chamber. The rapid depletion leads to a short operational time and a high variability in powder delivery rate. FIG. 3B depicts a prior art device with a large diameter delivery conduit. FIG. 3C illustrates that a delivery conduit outlet with a large aperture has a lower powder delivery rate that slowly depletes the quantity of powder material in the mixing chamber. The slow depletion leads to a longer operational time and a slower variability in powder delivery rate. FIG. 3C shows that prior art devices with fixed delivery conduit diameters have large variations in powder perturbation consistency over the operational time of the device.

As shown in FIGS. 1, 2, and 3, perturbation rates of prior art simple air abrasion devices are dependent on the 1) amount of material depleted from the device, 2) length of the delivery conduit, 3) diameter and apertures of the delivery conduits. Prior art simple air abrasion devices compensate for this deficiency by requiring the user to constantly adjust the inlet gas pressure. Adjustment of the inlet supply gas pressure controls the flow rates through the device and therefore the inlet air velocities. Higher inlet air velocities allow for increase in material perturbation at greater distances between the delivery conduit outlet and the powder material. Therefore, over the operational time of the instrument, the user must adjust the input pressure to compensate for the decline in powder delivery rate. Additionally, since the inlet pressure is utilized to control the powder delivery rate, the user must also modify the input pressure to select the perturbation intensity for the required procedure.

Consequently, since low perturbation rates are only achieved at lower supply pressures, the user must operate at lower pressures for procedures that require reduced powder delivery rates. As the powder delivery rate of the device is reduced, the efficiency of the device decreases since the abrasive powder is delivered at lower nozzle velocities.

The invention disclosed herein solves the following shortcomings with the prior art simple self-contained air abrasion devices:
1) Introduces new means for maintaining a consistent powder delivery rate without adjustment to the input pressure.
2) Introduces new means for selecting the powder delivery rate without adjustment to the input pressure.
3) Enhances operational efficiency by providing simple means for delivering lower powder delivery rates at high input pressures.

In addition, this invention teaches a new innovative method for providing a reliable perturbation rate selection via an external bypass tube.

BRIEF SUMMARY OF THE INVENTION

Accordingly, several objects and advantages of the present invention are to:
1) Provide means for a consistent powder delivery rate over the operational time of the device.
2) Provide means for a consistent powder delivery rate independently of the inlet gas pressure.
3) Provide means for selecting the powder delivery rate independently of the inlet gas pressure.
4) Provide means for low powder delivery rates at high supply pressures.
5) To provide a simple control method for selecting the powder delivery rate.
6) To provide a connector based adjustment for powder delivery rate.

In addition, this invention teaches new innovative methods for providing precise powder concentration selection and delivery rate consistency while maintaining optimal operational efficiency.

SUMMARY OF CLAIMS (AS FILED)

According to an embodiment of the invention, a micro-abrasive blasting device, may comprise:
  a chamber having a side wall, a first end wall at one end of the chamber and a second end wall at an opposite end of the chamber;
  a quantity of abrasive powder disposed within said chamber;
  a gas-receiving port in said end wall;
  a delivery conduit disposed within the chamber and extending in fluid communications from said gas-receiving port to delivery conduit outlet towards said abrasive powder;
  a discharge port in said chamber wall;
  a discharge conduit elongated from a discharge conduit inlet to a discharge conduit outlet and extending in fluid communications through said discharge port external to the chamber;
  wherein the positioning of said delivery conduit outlet with respect to said abrasive powder controls the quantity of abrasive powder introduced into the gas stream.

Adjustment of said delivery conduit outlet aperture provides control over the quantity of abrasive powder introduced into the gas stream.

According to an embodiment of the invention, a micro-abrasive blasting device may comprise:
  a chamber having a side wall, a first end wall at one end of the chamber and a second end wall at an opposite end of the chamber;
  a quantity of abrasive powder disposed within said chamber;
  a gas-receiving port in said end wall;
  a delivery conduit disposed within the chamber and extending in fluid communications from said gas-receiving port to delivery conduit outlet towards said abrasive powder;

a discharge port in said chamber wall;
a discharge conduit elongated from a discharge conduit inlet to a discharge conduit outlet and extending in fluid communications through said discharge port external to the chamber;
wherein adjustment of said delivery conduit outlet aperture provides control over the quantity of abrasive powder introduced into the gas stream.

The positioning of said delivery conduit outlet with respect to said abrasive powder controls the quantity of abrasive powder introduced into the gas stream.

According to an embodiment of the invention, a micro-abrasive blasting device, may comprise:
a chamber having a side wall, a first end wall at one end of the chamber and a second end wall at an opposite end of the chamber;
a quantity of abrasive powder disposed within said chamber;
a plurality of gas-receiving ports in said end wall;
a plurality delivery conduits disposed within the chamber and extending in fluid communications from said gas-receiving ports to delivery conduit outlets towards said abrasive powder;
a discharge port in said chamber wall;
a discharge conduit elongated from a discharge conduit inlet to a discharge conduit outlet and extending in fluid communications through said discharge port external to the chamber;
wherein at least two said delivery conduit outlets support unique positions with respect to said abrasive powder disposed within the chamber.

Flow through at least one delivery conduit is selectable.

At least two delivery conduit outlets support unique apertures.

According to an embodiment of the invention, a micro-abrasive blasting device, may comprise:
a distribution chamber having a third end wall disposed opposite said second end wall;
a distribution chamber inlet port disposed in said third end wall;
wherein pressurized-gas provided at said distribution chamber inlet port is distributed through said distribution chamber to said gas-receiving ports.

A powder containment filter may be disposed within the distribution chamber;
wherein said powder containment filter prevents said powder material from exiting said micro-abrasive blasting device via said distribution chamber inlet port.

At least one bypass conduit outlet port is disposed within the distribution chamber wall;
at least one bypass conduit inlet port is disposed within the distribution chamber wall;
at least one bypass conduit extends from said bypass conduit outlet port external to the distribution chamber and back into the distribution chamber through said bypass conduit inlet port and terminates at said gas-receiving port;
wherein opening and closing of bypass conduit external to the distribution chamber controls the quantity of abrasive powder introduced into the gas stream.

According to an embodiment of the invention, a micro-abrasive blasting device, may comprise:
a chamber having a side wall, a first end wall at one end of the chamber and a second end wall at an opposite end of the chamber;
a quantity of abrasive powder disposed within said chamber;
a plurality of gas-receiving ports in said first end wall;
a plurality of delivery conduits disposed within the chamber and extending in fluid communications from said gas-receiving ports to delivery conduit outlets towards said abrasive powder;
a discharge port in said second chamber wall;
a discharge conduit elongated from a discharge conduit inlet to a discharge conduit outlet and extending in fluid communications through said discharge port external to the chamber;
wherein said delivery conduit outlets support at least two unique apertures.

Flow through at least one delivery conduit is selectable.

Said delivery conduit outlets support at least two unique positions with respect to abrasive powder disposed within the chamber.

At least two delivery conduit outlets support unique positions with respect to abrasive powder disposed within the chamber.

The device comprises:
a distribution chamber having a third end wall disposed opposite said second end wall;
a distribution chamber inlet port disposed in said third end wall;
wherein pressurized-gas provided at said distribution chamber inlet port is distributed through said distribution chamber to said gas-receiving ports.

A powder containment filter is disposed within the distribution chamber; wherein said powder containment filter prevents said abrasive powder from exiting said micro-abrasive blasting device via said distribution chamber inlet port.

According to an embodiment of the invention, a micro-abrasive blasting device, may comprise:
a chamber having a side wall, a first end wall at one end of the chamber and a second end wall at an opposite end of the chamber;
a quantity of abrasive powder disposed within said chamber;
a plurality of gas-receiving ports in said first end wall;
a plurality of delivery conduits disposed within the chamber and extending in fluid communications from said gas-receiving ports to delivery conduit outlets towards said abrasive powder;
a discharge port in said second chamber wall;
a discharge conduit elongated from a discharge conduit inlet to a discharge conduit outlet and extending in fluid communications through said discharge port external to the chamber;

wherein said delivery conduit outlets support at least two unique apertures,
wherein:
a distribution chamber having a third end wall disposed opposite said second end wall;
a distribution chamber inlet port disposed in said third end wall;
wherein pressurized-gas provided at said distribution chamber inlet port is distributed through said distribution chamber to said gas-receiving ports;
wherein:
at least one bypass conduit outlet port is disposed within the third end wall;
at least one bypass conduit inlet port is disposed within the third end wall;
at least one bypass conduit extends from said bypass conduit outlet port external to the distribution chamber and back into the distribution chamber through said bypass conduit inlet port and terminates at said gas-receiving port;

wherein opening and closing of bypass conduit external to the distribution chamber controls the quantity of abrasive powder introduced into the gas stream.

BRIEF DESCRIPTION OF THE SEVERAL VIEWS OF THE DRAWING

Various other objects, advantages, and features of the invention will become apparent to those skilled in the art from the following discussion taken in conjunction with the following drawings, where closely related figures have the same number but different alphabetic suffixes:

FIGS. 1, 2, and 3 are views of prior art micro-abrasive blasting device.

FIGS. 4 and 5 are views of micro-abrasive blasting devices with adjustable delivery conduit outlet location.

FIGS. 8, 9, and 10 are views of micro-abrasive blasting devices with plurality of delivery conduits that control the perturbation intensity.

FIG. 12 is a view of the preferred micro-abrasive blasting device with an external bypass conduit that controls the perturbation intensity.

REFERENCE NUMERALS IN DRAWINGS

Figure 2A:
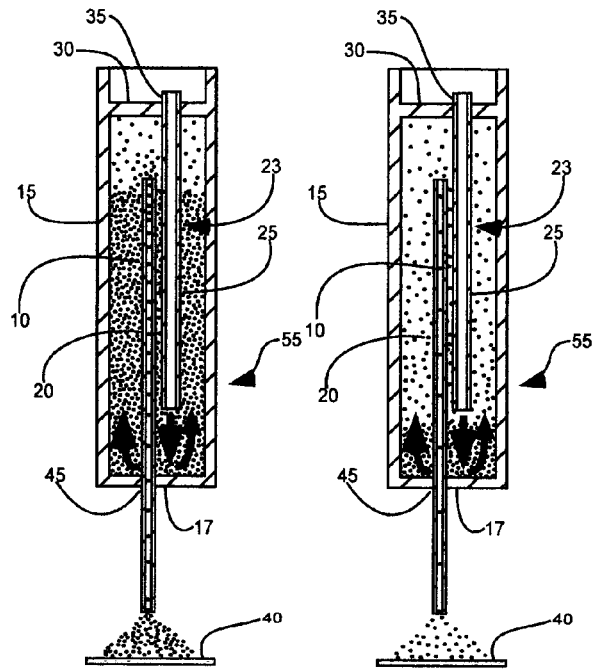
Figure 2B:
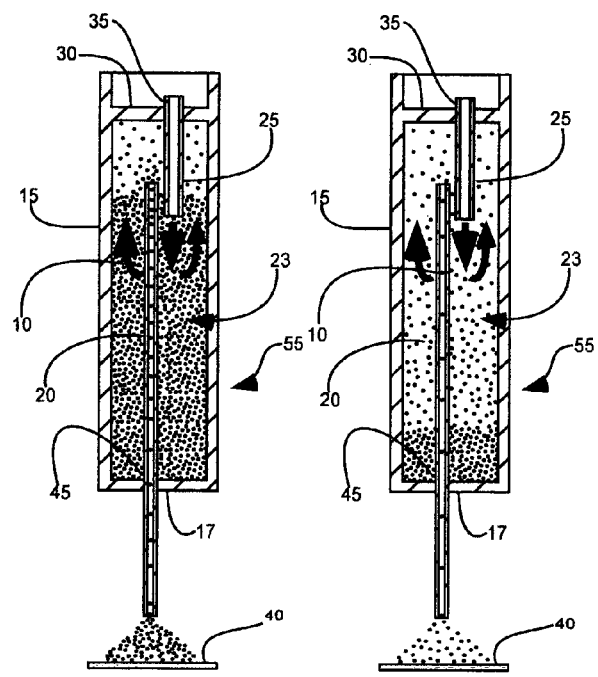
Figure 2C:
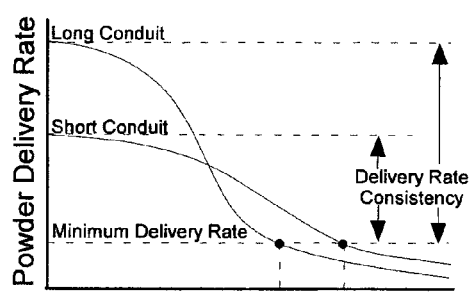
Figures 3A, 3B:
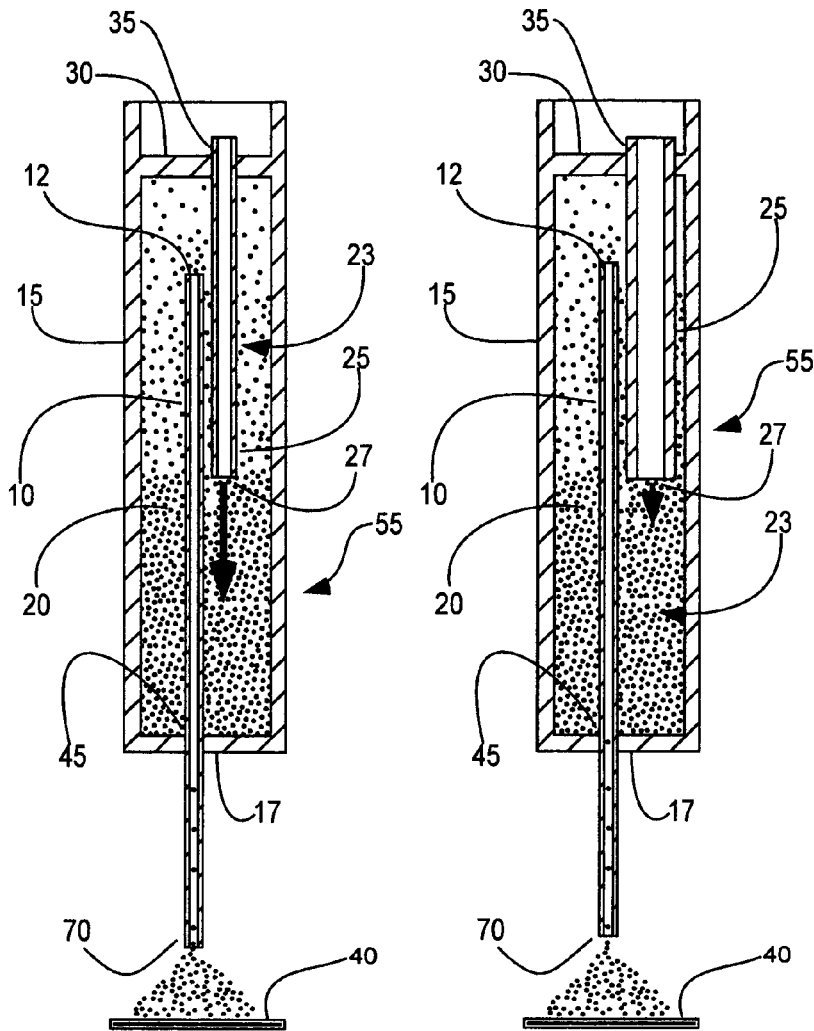
Figure 3C:
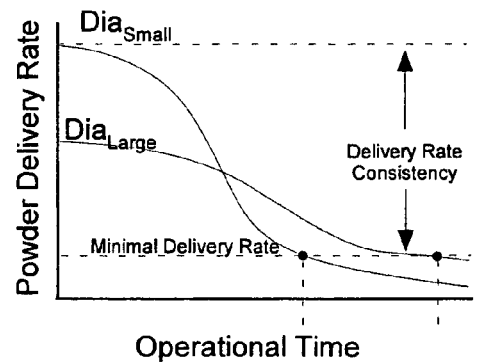

| | |
|---|---|
| 10 | discharge conduit |
| 12 | discharge conduit inlet |
| 15 | mixing chamber side wall |
| 17 | mixing chamber first end wall |
| 20 | powder material |
| 23 | mixing chamber |
| 25 | delivery conduit |
| 27 | delivery conduit outlet |
| 30 | mixing chamber second end wall |
| 35 | gas-receiving port |
| 40 | target material |
| 45 | discharge port |
| 50 | delivery conduit inlet |
| 55 | micro-abrasive blasting device |
| 60 | mixing chamber third end wall |
| 65 | distribution chamber |
| 70 | discharge conduit outlet |
| 75 | distribution chamber inlet port |
| 85 | bypass conduit |
| 90 | bypass conduit outlet port |
| 93 | bypass conduit inlet port |
| 97 | powder containment filter |
| 99 | bypass conduit pinch valve |

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various FIGURES are designated by the same reference numerals.

Referring to FIG. 4A, a micro-abrasive blasting device 55 is disclosed. Micro-abrasive blasting device 55 includes a mixing chamber 23 having a mixing chamber side wall 15, a first end wall 17, and a second end wall 30. A abrasive powder material 20 is disposed in mixing chamber 23.

A gas-receiving port 35 is disposed in mixing chamber second end wall 30. A delivery conduit 25 is in fluid communications with gas-receiving port 35, and extends through gas-receiving port 35 into mixing chamber 23. Delivery conduit 25 terminates at delivery conduit outlet 27.

A discharge port 45 is disposed in mixing chamber second end wall 30. A discharge conduit 10, elongated from discharge conduit inlet 12 to discharge conduit outlet 70, extends in fluid communications through discharge port 45 external to mixing chamber 23.

As pressurized-gas is supplied to micro-abrasive blasting device 55 through gas-receiving port 35, gas flows via delivery conduit 25 and out of delivery conduit outlet 27 into mixing chamber 23. As flow is initiated, powder material 20 instantaneously mixes with the flowing gas and is dispensed through discharge conduit 10 to strike target material 40.

FIG. 4A shows blasting device 55 in its initial operational state, when powder material 20 is still plentiful in mixing chamber 23. As powder material 20 is discharged during operation, the quantity of powder material 20 in mixing chamber 23 is reduced. Referring to FIGS. 4B and 4C, delivery conduit 25 is movable with respect to gas-receiving port 35 to maintain the location of delivery conduit outlet 27 constant with respect to powder material 20 as it is depleted from mixing chamber 23. As the quantity of powder material 20 is reduced, the position of gas-delivery conduit outlet 27 progressively protrudes further into mixing chamber 23 in order to maintain a consistent gas flow perturbation onto powder material 20. As shown in FIG. 4D, the adjustment of delivery conduit outlet 27 positions significantly enhances the perturbation consistency of powder material 20 and therefore the powder delivery rate. FIG. 4D compares the powder delivery rate when gas-delivery conduit outlet 27 positions are fixed and variable. Significant increase in consistency of powder delivery rate is demonstrated over prior art devices with a fixed position of delivery conduit outlet 27.

Figures 5A, 5B, 5C:
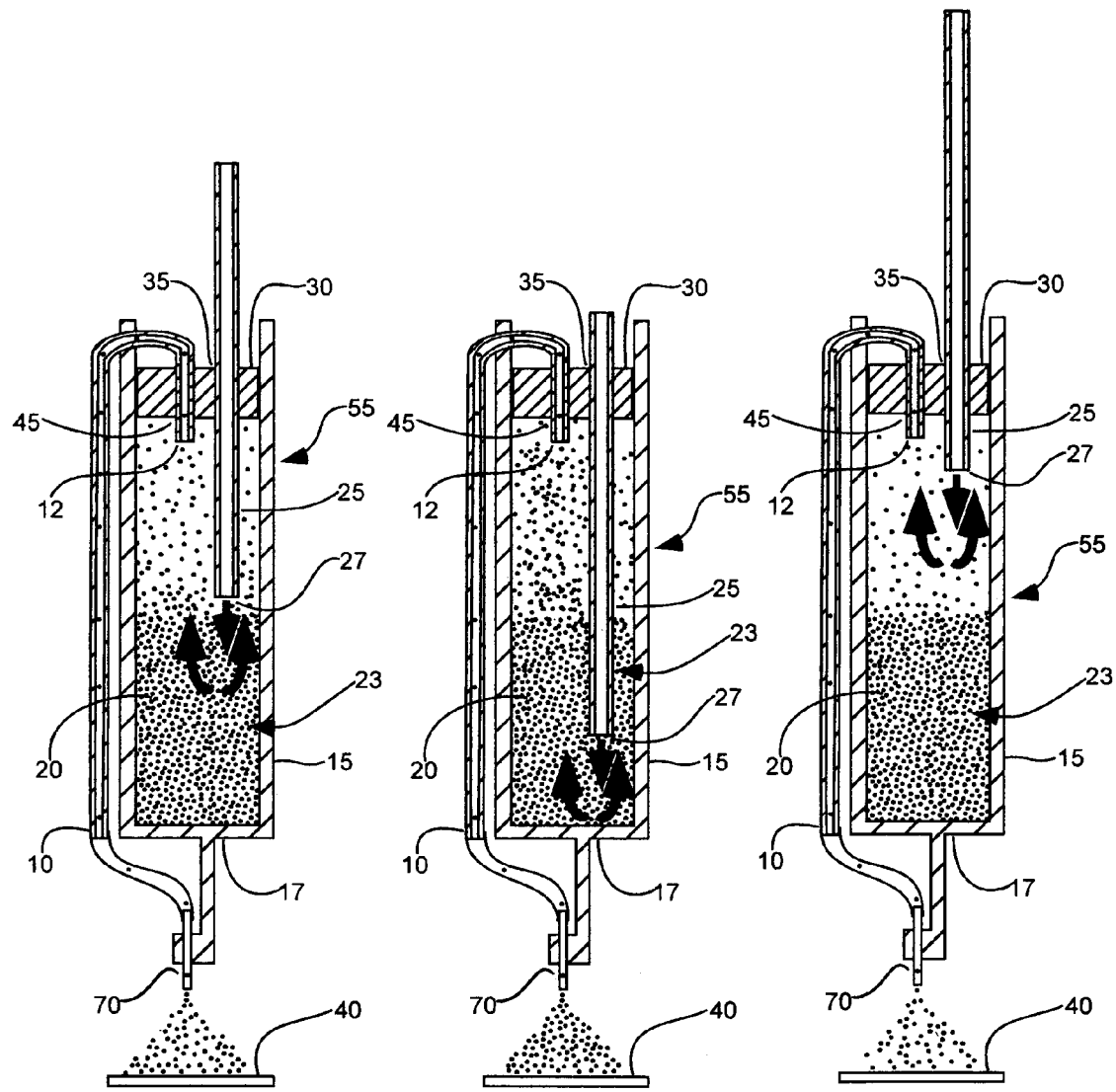

The embodiment of FIG. 5 demonstrates how the relative position of gas-delivery conduit outlet 27 with respect to powder material 20 is utilized to select the powder delivery rate. Referring to FIG. 5, the embodiment of FIG. 4 is also utilized to provide selection of powder delivery rate by varying the positioning of delivery conduit outlet 27 with respect to powder material 20. Referring to FIGS. 5A and 5B, when a high perturbation rate of powder material 20 is required, delivery conduit 25 is positioned so delivery conduit outlet 27 is close to or imbedded within powder material 20. Referring to FIG. 5C, when a reduced quantity of powder material 20 is required, delivery conduit 25 is positioned so delivery conduit outlet 27 is distant from powder material 20.

When delivery conduit 25 is distant from powder material 20, less perturbation of powder material in mixing chamber 23 is generated since the velocity of the gas-flow is decreased significantly by the time it reaches powder material 20. The embodiment of FIG. 5 shows how the relative position of gas-delivery conduit outlet 27 with respect to powder material 20 also provides means for selecting the perturbation rate.

The embodiment of FIGS. 4 and 5 demonstrate how the positioning of delivery conduit outlet 27 provides means for both selecting and controlling the powder delivery rate over the operational time of blasting device 55 independently of the inlet gas pressure. Controlling the location of gas-delivery conduit outlet 27 with respect to the powder material 20 provides a powerful method for optimizing the performance of self-contained air abrasion devices.

Referring to the embodiment of FIG. 6, blasting device 55 is provided with means of adjusting the diameter of delivery conduit 25, and thereby the aperture of gas-delivery conduit outlet 27. Adjustment of delivery conduit outlet 27 aperture is utilized to control powder material 20 perturbation rates. As gas-delivery conduit outlet 27 aperture increases the velocity of the gas-flow into mixing chamber 23 decreases, while conversely as the gas-delivery conduit outlet 27 aperture decreases the velocity of the gas-flow into mixing chamber 23 increases. Higher gas-flow velocities out of gas-delivery conduit outlet 27 generate increased perturbation of powder material 20 and greater powder delivery rate. Conversely, lower gas-flow velocities out of gas-delivery conduit outlet 27 lead to decreased perturbation of powder material 20 and lower powder delivery rate.

Figure 6A:
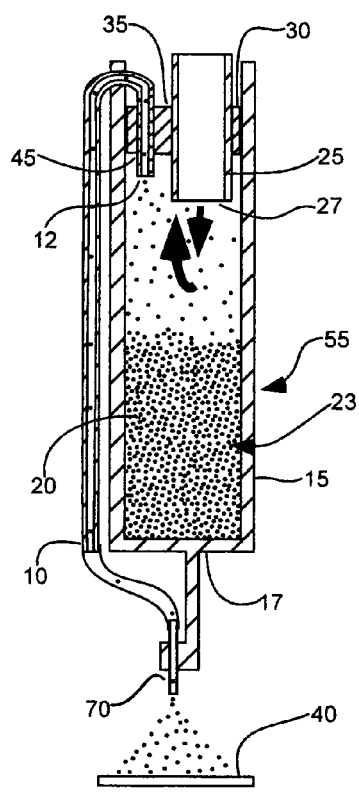
FIG. 6 is a view of a micro-abrasive blasting device with adjustable delivery conduit outlet aperture.

Referring to FIG. 6A, delivery conduit outlet 27 is adjusted to have a large aperture to provide lower inlet velocity into mixing chamber 23. The low inlet velocity at delivery conduit outlet 27 provides low perturbation rates to powder material 20. Since the low inlet gas stream velocity generates low momentum to the gas, the gas is able to quickly change direction and exit mixing chamber 23 via discharge conduit inlet 12.

Figure 6B:
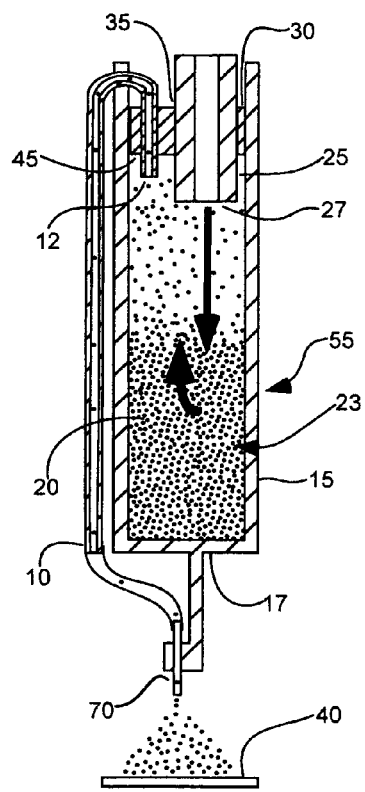
Figure 6C:
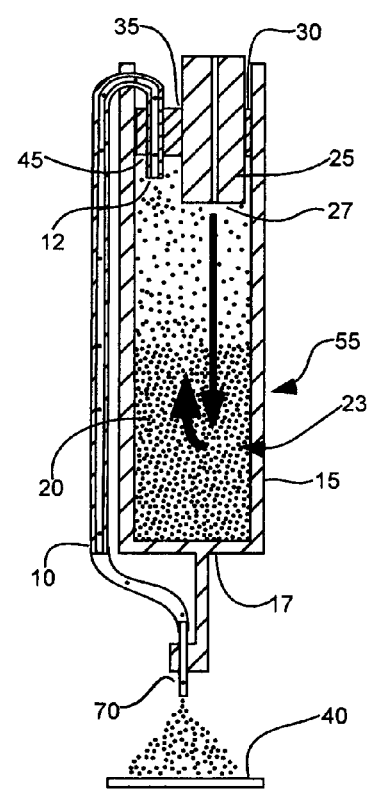

Referring to FIGS. 6B and 6C, as the delivery conduit outlet 27 aperture is adjusted to be smaller, the inlet velocities into mixing chamber 23 of the gas at delivery conduit outlet 27 increase. The increase in the inlet gas stream velocity generates greater momentum to the gas. The gas is able to less rapidly change direction and exit mixing chamber 23 via discharge conduit inlet 12. The greater gas momentum carries the gas further into mixing chamber 23. As the gas travels further into mixing chamber 23, it increases the perturbation of powder material 20, and therefore the perturbation rates.

Similarly, the adjustment of the delivery conduit outlet 27 aperture of the embodiment in FIG. 6 may be utilized to maintain a consistent abrasive perturbation. When powder material 20 is plentiful in mixing chamber 23, setting delivery conduit outlet 27 aperture to large yields low gas-flow velocities into powder material 20. As powder material 20 is depleted from mixing chamber 23, delivery conduit outlet 27 aperture is decreased to generate a more rapid gas-flow velocity into mixing chamber 23. The resulting increase in gas-flow velocity maintains constant perturbation of powder material 20 over the operational time of blasting device 55.

In the same manner that variable delivery conduit outlet 27 aperture is utilized to control the powder delivery rate, adjustment of the gas-delivery conduit outlet 27 aperture also provides means for selecting the powder delivery rate. Therefore, the embodiment of FIG. 6 provides means for selecting and controlling the powder delivery rate over the operational life of blasting device 55 independently of the inlet gas pressure.

Many embodiments may be employed to provide means of adjustment to the delivery conduit outlet 27 aperture and location. However, the abrasive nature of powder material 20 provides a significant challenge to any moving components exposed to powder material 20 within mixing chamber 23.

FIG. 7 provides the preferred embodiment for achieving delivery conduit outlet 27 aperture adjustability externally to mixing chamber 23. Referring to FIG. 7, a plurality of delivery conduits 25 are in fluid communications with a plurality of gas-receiving ports 35 disposed in mixing chamber second end wall 30. Delivery conduits 25 may all support the same or different delivery conduit outlets 27 apertures. A single source of pressurized-gas supplies micro-abrasive blasting device 55 through gas-receiving ports 35, as gas flows via delivery conduits 25 and out of delivery conduit outlets 27 into mixing chamber 23. Means are provided for individually and selectively opening and closing each delivery conduit inlet 50.

Figures 7A, 7B, 7C:
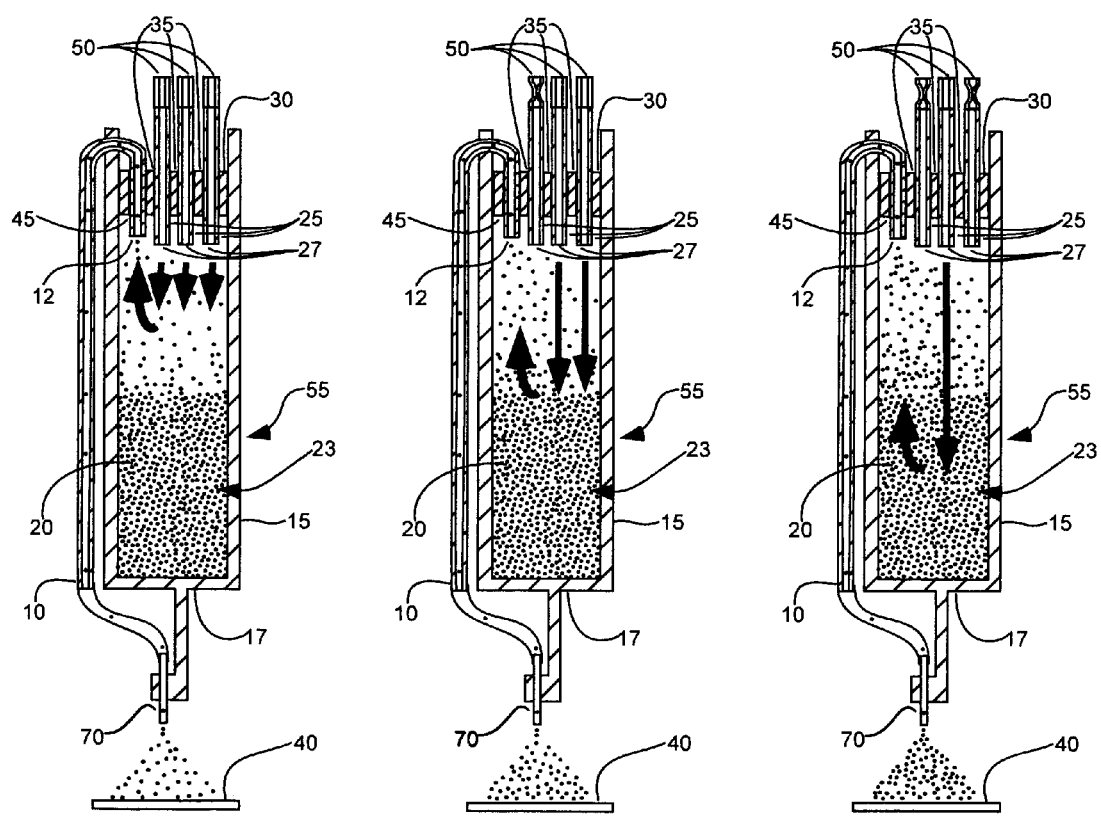
FIG. 7 is a view a micro-abrasive blasting device with plurality of delivery conduits that controls the overall delivery conduit outlet aperture.

The velocity of the gas entering mixing chamber 23 is a function of the sum of delivery conduit outlets 27 apertures. As shown in FIG. 7A, when all delivery conduits 25 are open the gas flows through all the delivery conduit outlets 27. Having all apertures of delivery conduit outlets 27 open provides a large overall aperture for the single gas source and therefore lower inlet gas velocities. As shown in FIGS. 7B and 7C, as some delivery conduits 25 are selectively closed at delivery conduit inlets 50, the number of operational delivery conduit outlets 27 is reduced, and therefore the effective overall aperture is reduced. The reduction in aperture due to selective closing of delivery conduits 25, leads to increase in the inlet gas stream velocity. Preferred embodiment of FIG. 7 provides means for controlling the gas stream velocity into mixing chamber 23 and therefore the perturbation rates of powder material 20.

Referring to FIG. 8, the plurality of delivery conduits 25 of the preferred embodiment of FIG. 7, support a plurality of lengths that position delivery conduit outlets 27 at various positions with respect to powder material 20. By selectively permitting gas flow through individual delivery conduits 25, control over the powder material 20 perturbation rates is achieved.

Figures 8A, 8B, 8C:
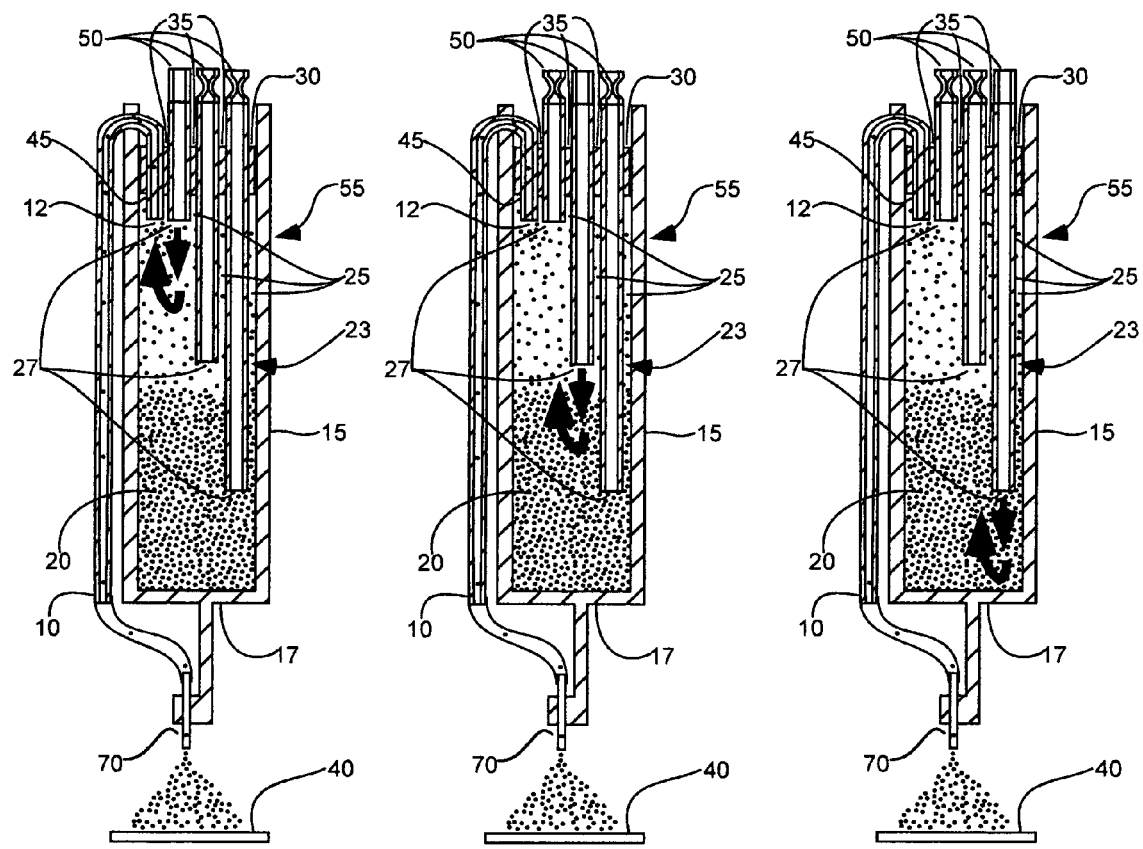

Referring to FIG. 8A, when a reduced quantity of powder material 20 is required, the delivery conduit 25 with delivery conduit outlet 27 distant from the powder material 20 is opened for gas flow. Referring to FIGS. 8B and 8C, when a more aggressive perturbation is required, delivery conduit 25 with delivery conduit outlet 27 that is closer to or imbedded within the powder material 20 is opened for gas flow.

Figure 9A:
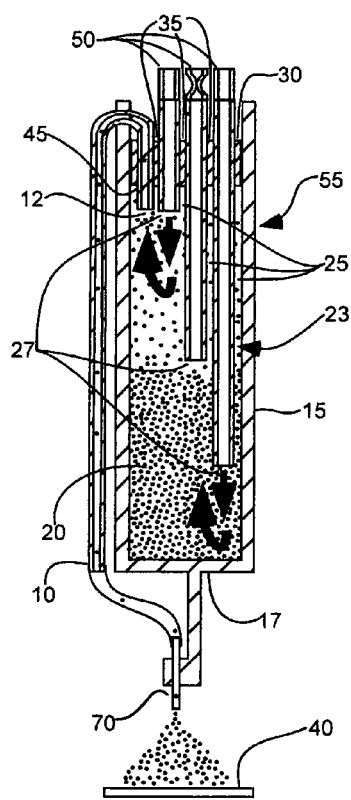
Figure 9B:
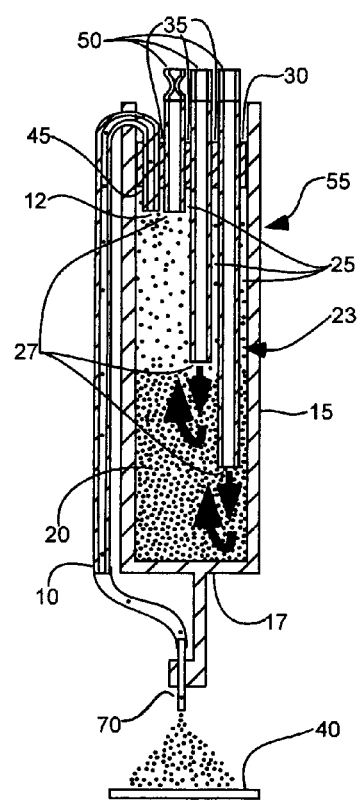
Figure 9C:
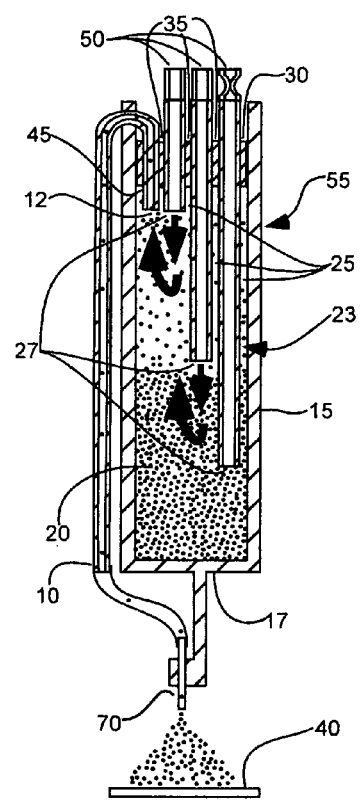

Additionally, as powder material 20 is depleted from mixing chamber 23, longer reaching delivery conduits 25 maybe individually selected to create consecutive approximations in order to maintain a constant position of delivery conduit outlets 27 with respect to powder material 20. This provides means of generating a consistent powder delivery rate over the operational time of blasting device 55 as powder material 20 is depleted from mixing chamber 23. Therefore, the plurality of delivery conduits 25 of various lengths is utilized to replace the movable delivery conduit 25 of the embodiment of FIGS. 4 and 5.

Referring to FIGS. 9 and 10, selective opening and closing of delivery conduits 25 provides operational control over both the location of the delivery conduit outlets 27 and apertures of delivery conduit outlets 27. Design choices of delivery conduits 25 lengths and delivery conduit outlets 27 apertures provide an infinite number of configurations for optimizing the perturbation consistency of micro-abrasive blasting device 55. Selection of delivery conduits 25 during operation, provide the user with full control over the perturbation rate of the device. The selective opening and closing of delivery conduits 25 provide means for providing consistent powder delivery rate at all perturbation intensities independently of the input gas pressure.

FIG. 9 shows how opening of multiple delivery conduits 25 simultaneously provides means for selecting the perturbation intensity while optimizing the powder delivery consistency. FIG. 10 shows how combinations of various delivery conduits 25 lengths that support various delivery conduit outlets 27 apertures are utilized to select the perturbation intensity while optimizing the powder delivery consistency.

Figure 11A:
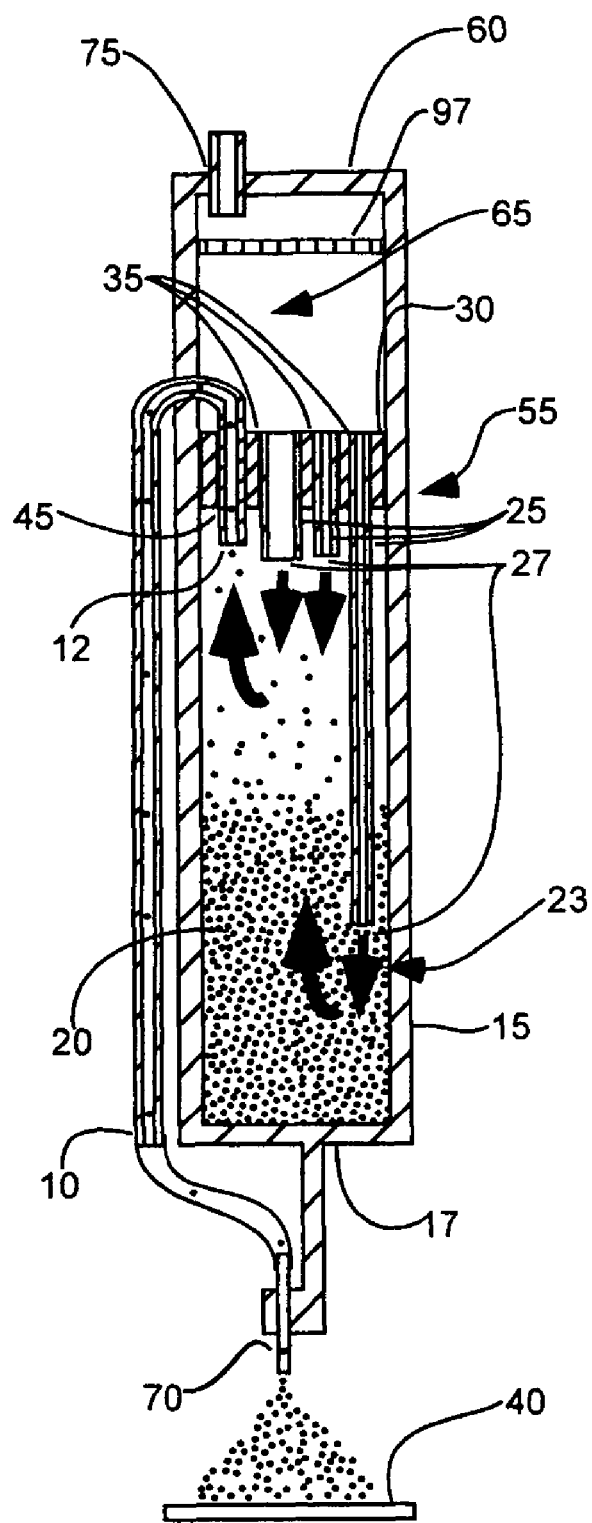
FIG. 11 is a view a micro-abrasive blasting device with a gas distribution chamber and powder containment filter.

Referring to FIG. 11, mixing chamber third end wall 60 is disposed opposite mixing chamber second end wall 30, to form distribution chamber 65. Distribution chamber inlet port 75 is disposed in mixing chamber third end wall 60. The single source pressurized-gas is supplied to micro-abrasive blasting device 55 through distribution chamber inlet port 75 into distribution chamber 65. The pressurized-gas passes through distribution chamber 65 and gas-receiving ports 35 via delivery conduits 25 out of delivery conduit outlets 27 into mixing chamber 23. A powder containment filter 97 is disposed within distribution chamber 65 to prevent powder material 20 from exiting micro-abrasive blasting device 55 via distribution chamber inlet port 75. Similarly to the embodiments of FIGS. 9 and 10, opening and closing of delivery conduits 25 provides superior control, consistency, and selectivity of the perturbation rates.

FIG. 12 is the preferred embodiment for selecting and controlling the perturbation rate of mixing chamber 23 externally to micro-abrasive blasting device 55. A bypass conduit outlet port 90 and bypass conduit inlet port 93 is disposed in mixing chamber third end wall 60 of distribution chamber 65. A bypass delivery conduit 85 extends from bypass conduit outlet port 90 out of distribution chamber 65. Bypass delivery conduit 85 loops back into distribution chamber 65 via bypass conduit inlet port 93 to terminate in fluid communications with gas-receiving port 35.

As pressurized gas is delivered to distribution chamber 65 via distribution chamber inlet port 75, it flows equally through all gas-receiving ports 35 and bypass conduit outlet port 90. When gas is permitted to flow through bypass conduit 85, the overall aperture opening of delivery conduits 25 is large leading to low inlet gas velocities at delivery conduit outlets 27.

However, once bypass conduit pinch valve 99 is closed, flow is restricted from passing through bypass conduit 85, therefore reducing the overall aperture openings of delivery conduits 25. The reduced overall delivery conduit outlets 27 aperture leads to higher inlet gas velocities and therefore greater perturbation rate.

The preferred embodiment of FIG. 12 provides means for externally controlling the perturbation rates generated within mixing chamber 23.

FIG. 12 shows micro-abrasive blasting device 55 with a single delivery conduit 25 supporting a bypass conduit 85. However, a plurality of delivery conduits 25 supporting a plurality of bypass conduits 85 can be employed to provide external control to delivery conduits of various lengths and apertures.

Of course, the actuation of bypass conduit pinch valve 99 in the preferred embodiment of FIG. 12 can simply be integrated into the pressurized-gas supply connector. Such a mechanism would provide the user with simple means for selecting which delivery conduits are open and closed, thereby providing the user with external means of controlling the perturbation rates internal to mixing chamber 23.

From the description above, the following advantages of the present invention become evident:

(a) Ability to select the powder delivery rate independently of the inlet gas pressure.

(b) Ability to deliver consistent powder perturbation rate independently of the supply gas pressure.

(c) Ability to select the powder delivery rate independent of the quantity of powder material remaining in the mixing chamber.

(d) Ability to control and select the perturbation rate externally to the mixing chamber.

(e) Ability to deliver low perturbation rates at high inlet gas pressures.

While the invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

SUMMARY, RAMIFICATION, AND SCOPE

The present invention accomplishes the above-stated objectives, as well as others, as may be determined by a fair reading and interpretation of the entire specification.

Accordingly, the reader will see that the present invention is a micro-abrasive blasting device with superior perturbation control and powder flow rate consistency because of the ability to individually select from a plurality of delivery conduits of various lengths and apertures.

Furthermore, the present invention has the additional advantages in that it provides the user with ability to select powder delivery rates by external manipulation of the delivery conduits openings.

it provides the device designer with many options for optimizing the performance of the instrument for maximum efficiency.

it provides a reliable device that delivers a consistent quantity of abrasive over the entire operational time of the instrument.

Thus the scope of the invention should be determined by the appended claims and their legal equivalents, rather than by the examples given.

What I claim as my invention is:

1. A micro-abrasive blasting device, comprising:

a chamber having a side wall, a first end wall at one end of the chamber and a second end wall at an opposite end of the chamber;

a quantity of abrasive powder disposed within said chamber;

a plurality of gas-receiving ports in said second end wall;

a plurality of delivery conduits disposed within the chamber and extending in fluid communications from said gas-receiving ports to delivery conduit outlets towards said abrasive powder, for perturbating the abrasive powder;

a discharge port in said second end wall;

a discharge conduit elongated from a discharge conduit inlet to a discharge conduit outlet and extending in fluid communications through said discharge port external to the chamber;

wherein said delivery conduit outlets comprise at least two different apertures.

2. The device, according to claim 1, wherein:

flow through at least one delivery conduit is selectable.

3. The device, according to claim 2, wherein:

said delivery conduit outlets support at least two unique positions with respect to abrasive powder disposed within the chamber.

4. The device, according to claim 1, wherein:
at least two delivery conduit outlets support unique positions with respect to abrasive powder disposed within the chamber.

5. The device, according to claim 4, wherein:
flow through at least one delivery conduit is selectable.

6. The device, according to claim 1, wherein:
a distribution chamber having a third end wall disposed opposite said second end wall;
a distribution chamber inlet port disposed in said third end wall;
wherein pressurized-gas provided at said distribution chamber inlet port is distributed through said distribution chamber to said gas-receiving ports.

7. The device, according to claim 6, wherein:
a powder containment filter is disposed within the distribution chamber;
wherein said powder containment filter prevents said abrasive powder from exiting said micro-abrasive blasting device via said distribution chamber inlet port.

8. A micro-abrasive blasting device, comprising:
a chamber having a side wall, a first end wall at one end of the chamber and a second end wall at an opposite end of the chamber;
a quantity of abrasive powder disposed within said chamber;
a plurality of gas-receiving ports in said second end wall;
a plurality of delivery conduits disposed within the chamber and extending in fluid communications from said gas-receiving ports to delivery conduit outlets towards said abrasive powder;
a discharge port in said second chamber wall;
a discharge conduit elongated from a discharge conduit inlet to a discharge conduit outlet and extending in fluid communications through said discharge port external to the chamber;
wherein said delivery conduit outlets support at least two unique apertures;
wherein:
a distribution chamber having a third end wall disposed opposite said second end wall;
a distribution chamber inlet port disposed in said third end wall;
wherein pressurized-gas provided at said distribution chamber inlet port is distributed through said distribution chamber to said gas-receiving ports;
wherein:
at least one bypass conduit outlet port is disposed within the third end wall;
at least one bypass conduit inlet port is disposed within the third end wall;
at least one bypass conduit extends from said bypass conduit outlet port external to the distribution chamber and back into the distribution chamber through said bypass conduit inlet port and terminates at said gas-receiving port;
wherein opening and closing of bypass conduit external to the distribution chamber controls the quantity of abrasive powder introduced into the gas stream.

9. A micro-abrasive blasting device, comprising:
a chamber having a side wall, a first end wall at one end of the chamber and a second end wall at an opposite end of the chamber;
a quantity of abrasive powder disposed within said chamber;
a plurality of gas-receiving ports in one of the first and second end walls;
a plurality of delivery conduits disposed within the chamber and extending in fluid communications from said gas-receiving ports to delivery conduit outlets towards said abrasive powder;
a discharge port in one of the first and second end walls;
a discharge conduit elongated from a discharge conduit inlet to a discharge conduit outlet and extending in fluid communications through said discharge port external to the chamber;
wherein said delivery conduit outlets support at least two unique apertures;
wherein:
a distribution chamber having a third end wall disposed opposite said second end wall;
a distribution chamber inlet port disposed in said third end wall;
wherein pressurized-gas provided at said distribution chamber inlet port is distributed through said distribution chamber to said gas-receiving ports;
wherein:
at least one bypass conduit outlet port is disposed within the third end wall;
at least one bypass conduit inlet port is disposed within the third end wall;
at least one bypass conduit extends from said bypass conduit outlet port external to the distribution chamber and back into the distribution chamber through said bypass conduit inlet port and terminates at said gas-receiving port;
wherein opening and closing of bypass conduit external to the distribution chamber controls the quantity of abrasive powder introduced into the gas stream.

10. The device, according to claim 9, wherein both of the plurality of gas-receiving ports and the discharge port are disposed in the same one of the first and second end walls.

* * * * *